(12) United States Patent
Ikeda et al.

(10) Patent No.: US 11,579,215 B2
(45) Date of Patent: Feb. 14, 2023

(54) SAMPLE ANALYZER

(71) Applicant: CANON MEDICAL SYSTEMS CORPORATION, Otawara (JP)

(72) Inventors: Naru Ikeda, Otawara (JP); Yusuke Honnami, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 49 days.

(21) Appl. No.: 17/155,448

(22) Filed: Jan. 22, 2021

(65) Prior Publication Data

US 2021/0231756 A1 Jul. 29, 2021

(30) Foreign Application Priority Data

Jan. 28, 2020 (JP) .............................. JP2020-011943

(51) Int. Cl.
*G01R 33/12* (2006.01)
*G01N 33/543* (2006.01)

(52) U.S. Cl.
CPC ... *G01R 33/1276* (2013.01); *G01N 33/54326* (2013.01)

(58) Field of Classification Search
CPC ............... G01R 33/00; G01R 33/0035; G01R 33/0023; G01R 33/0017; G01R 31/3191; G01R 33/1276; G01B 7/004; G01C 17/38; G06F 3/017; G06F 3/0346; G06F 3/012; G01N 33/54326
See application file for complete search history.

(56) References Cited

U.S. PATENT DOCUMENTS

| | | | |
|---|---|---|---|
| 8,486,718 B2 | 7/2013 | Van Lankvelt et al. | |
| 9,274,104 B2 | 3/2016 | Tono et al. | |
| 9,658,219 B2 | 5/2017 | Verschuren et al. | |
| 10,317,399 B2 | 6/2019 | Ikeda et al. | |
| 2009/0096442 A1 | 4/2009 | Van Lankvelt | |
| 2009/0181856 A1 | 7/2009 | Van Lankvelt et al. | |
| 2009/0209042 A1 | 8/2009 | Van Lankvelt et al. | |
| 2011/0050215 A1* | 3/2011 | Kahlmann | H01F 7/0273 324/244 |
| 2015/0233908 A1* | 8/2015 | Kelly | G01N 33/54326 422/69 |
| 2017/0108495 A1 | 4/2017 | Ikeda et al. | |

FOREIGN PATENT DOCUMENTS

| | | |
|---|---|---|
| JP | 2009-536349 A | 10/2009 |
| JP | 2010-512531 A | 4/2010 |

(Continued)

*Primary Examiner* — Jermele M Hollington
*Assistant Examiner* — Taqi R Nasir
(74) *Attorney, Agent, or Firm* — Oblon, McClelland, Maier & Neustadt, L.L.P.

(57) ABSTRACT

A sample analyzer according to an embodiment includes a magnetic field applier configured to apply a magnetic field to a cartridge containing a sample and magnetic particles which bond an object to be detected in the sample; a measurer configured to measure the magnetic particles in the cartridge; and an analyzing processor configured to analyze and process a result of a measurement by the measurer. In addition, the magnetic field applier includes an electromagnet disposed on a first side of the cartridge; a magnetic member configured to be magnetized by the electromagnet; and a moving actuator configured to move the magnetic member.

17 Claims, 18 Drawing Sheets

(56) References Cited

FOREIGN PATENT DOCUMENTS

| | | |
|---|---|---|
| JP | 2010-212531 A | 9/2010 |
| JP | 2012-215553 A | 11/2012 |
| JP | 2017-75938 A | 4/2017 |
| WO | WO 2010/058303 A1 | 5/2010 |

* cited by examiner

US 11,579,215 B2

SAMPLE ANALYZER

CROSS REFERENCE TO RELATED APPLICATIONS

This application is based upon and claims the benefit of priority from the prior Japanese Patent Application No. 2020-011943, filed on Jan. 28, 2020, the entire contents of which are incorporated herein by reference.

FIELD

Embodiments described herein relate generally to sample analyzers.

BACKGROUND

Many hospitals are using sample analyzers that detect an object to be detected such as a very low amount of virus or living substance to enable early diagnosis of an infectious disease, for example. Such a sample analyzer includes a cartridge housing a sample containing an object to be detected and magnetic particles that are able to be specifically bonded with the object to be detected, for example, and counts the number of magnetic particles caught in a sensor area in the cartridge in order to highly sensitively detect and quantify the object to be detected contained in the sample.

In such a case, the sample analyzer may include an imager or an optical measurer as a measurer for measuring the object to be detected caught on the sensor area, thereby counting the number of magnetic particles. The arrangement of the measurer and a magnetic field applier needs to be carefully determined so that the magnetic field applier does not obstruct the measurer when the measurer measures the magnetic particles on the sensor area in the cartridge.

DETAILED DESCRIPTION

Sample analyzers according to embodiments will now be described with reference to the accompanying drawings. In the following descriptions, elements having substantially the same structure and functions have the same numerical symbol, and the explanation of such elements is repeated only when it is necessary to do so.

First Embodiment

Figure 1:
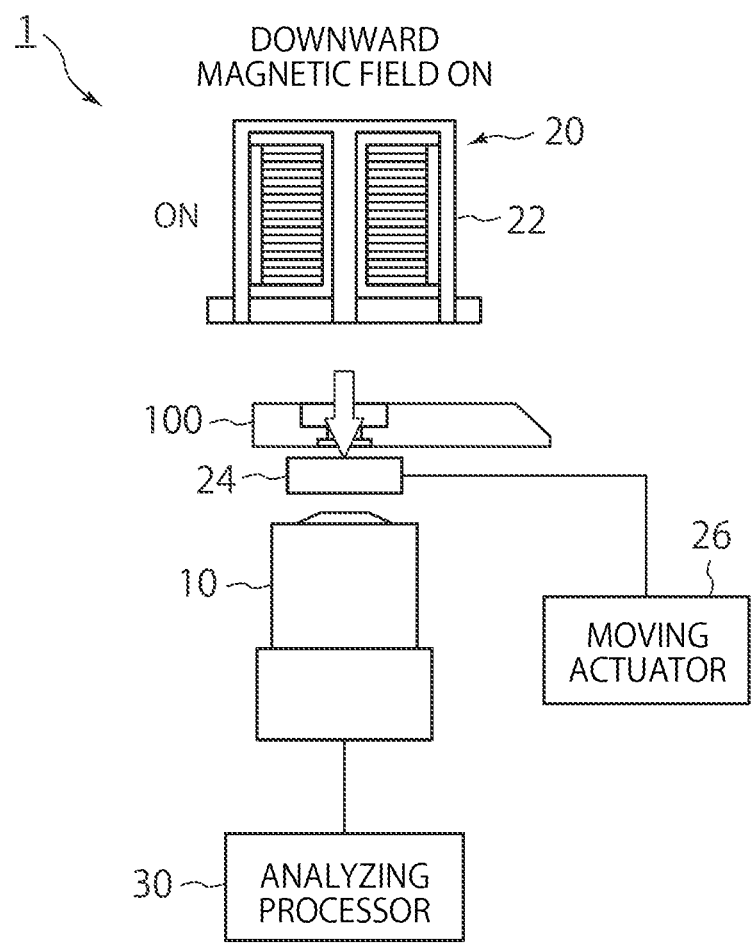
FIG. 1 illustrates a layout of a sample analyzer according to a first embodiment viewed from one side, for explaining the structure of the sample analyzer (a magnetic field is applied to move magnetic particles downward).
Figure 2:
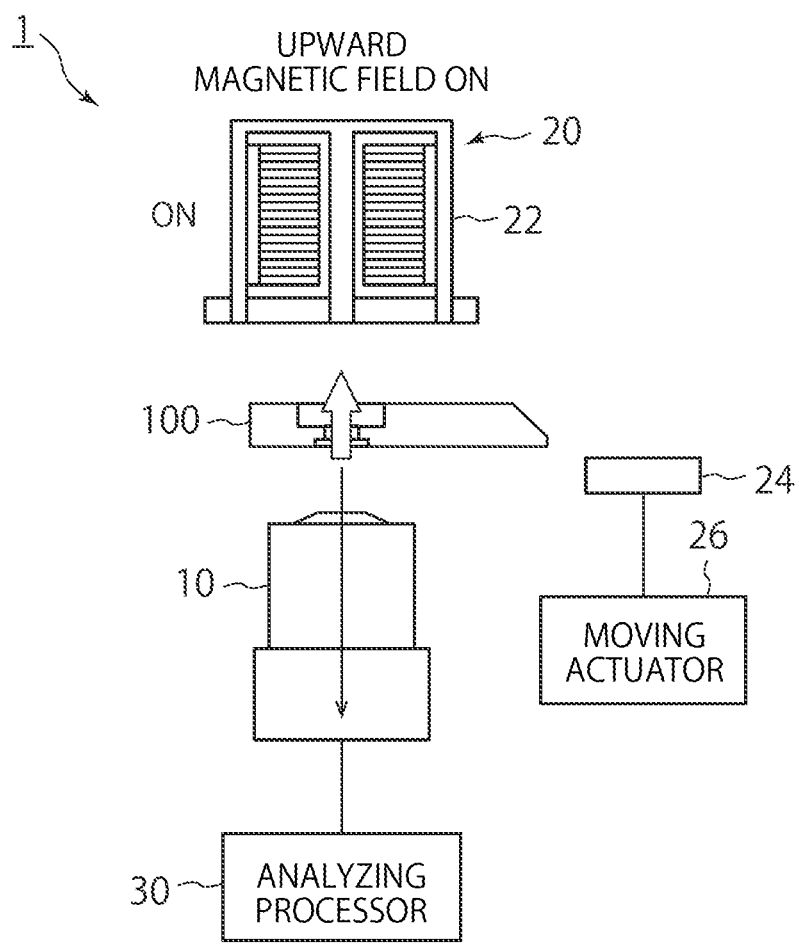
FIG. 2 illustrates a layout of the sample analyzer according to the first embodiment viewed from the one side, for explaining the structure of the sample analyzer (a magnetic field is applied to move the magnetic particles upward).

FIGS. 1 and 2 each illustrate a layout of a sample analyzer 1 according to a first embodiment viewed from one side, for explaining the structure of the sample analyzer. FIG. 1 is a layout diagram viewed from the one side, showing the state in which the sample analyzer 1 moves magnetic particles in a cartridge 100 downward. In FIG. 1, a magnetic member 24 is at a reversing position for reversing a gradient of a magnetic field generated by an electromagnet 22. FIG. 2 is a layout diagram viewed from the one side, showing the state in which the sample analyzer 1 moves the magnetic particles in the cartridge 100 upward. In FIG. 2, the magnetic member 24 is at a non-reversing position for not reversing the gradient of the magnetic field generated by the electromagnet 22.

As shown in FIGS. 1 and 2, the sample analyzer 1 according to the first embodiment includes an imager 10, a magnetic field applier 20, and an analyzing processor 30.

The imager 10 is an optical device that individually recognizes and counts magnetic particles bonded on a sensor area of the cartridge 100. The imager 10 may be, for example, an optical microscope or a microscopic imaging system including a combination of an optical microscope and a digital camera, for example. The sensor area of the cartridge 100 may be illuminated by such a method as epi-illumination, trans-illumination, bright-field illumination, or dark-field illumination generally used in optical microscopes. Examples of illumination light include lights generated by various types of lamps, lights filtered by optical filters for selecting wavelength, and lights from light emitting diodes (LED). Thus, the illumination means that is suitable for observing magnetic particles may be selected.

In the first embodiment, the imager 10 is located below the cartridge 100 set in the sample analyzer 1 in order to take an image of the sensor area of the cartridge 100. Furthermore, the imager 10 is located below the electromagnet 22 included in the magnetic field applier 20. The imager 10 corresponds to a measurer to measure the magnetic particles in the cartridge 100 in the sample analyzer 1 in the present embodiment.

The electromagnet 22 included in the magnetic field applier 20 may turn on or off the magnetic field. The electromagnet 22 may be a combination of permanent magnets or a combination of yokes and magnets. Any type of permanent magnet may be used to form the electromagnet 22. Any type of existing permanent magnet, such as ferrite magnet, Al—Ni—Co magnet, samarium-cobalt magnet, or Neodymium magnet, may be used. The electromagnet 22 is capable of preventing the magnetic field distribution from being distorted when the magnetic field is turned on or off, and capable of adjusting the intensity of the magnetic field. Regardless of the structure of the magnetic field applier 20, the magnetic field applier 20 is preferably arranged so that the magnetic pole of the magnetic field applier 20 faces the cartridge 100, and the SN axis of the magnetic poles are substantially orthogonal to a plane of the sensor area of the cartridge 100.

In the first embodiment, when the cartridge 100 is set on a support frame of the sample analyzer 1, the electromagnet 22 is above the cartridge 100. During the analysis of whether the object to be detected is contained in the sample, the cartridge 100 is inserted between the electromagnet 22 and the imager 10.

The magnetic field applier 20 also has a magnetic member 24 that is magnetized by the magnetic field applier 20. When the electromagnet 22 is turned on and starts generating a magnetic field, the magnetic member 24 is magnetized and acts as a magnet. The magnetic member 24 may be formed of a common soft magnetic material.

Figure 3:
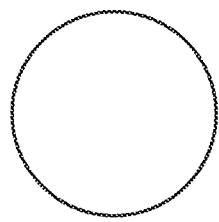
FIG. 3 illustrates a magnetic member included in the sample analyzer according to the first embodiment, viewed from above.
Figure 4:
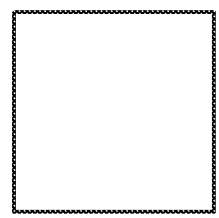
FIG. 4 illustrates another type of the magnetic member included in the sample analyzer according to the first embodiment, viewed from above.

The shape of the magnetic member 24 may be arbitrarily selected. In the first embodiment, the magnetic member 24 is preferably in a flat plate shape since when the magnetic member 24 is at the reversing position, it is located between the cartridge 100 and the imager 10. The shape of the magnetic member 24 viewed from above the sample analyzer 1 may also be arbitrarily selected. For example, the magnetic member 24 may be in a circular shape as shown in FIG. 3, or in a rectangular shape as shown in FIG. 4.

The magnetic field applier 20 further includes a moving actuator 26 that moves the magnetic member 24. The moving actuator 26 includes an actuator, for example, and moves the magnetic member 24 between the reversing position shown in FIG. 1 and the non-reversing position shown in FIG. 2. When the magnetic member 24 is at the reversing position shown in FIG. 1, the gradient of the magnetic field generated when the electromagnet 22 is turned on is reversed at the location of the cartridge 100. The reversing position is near the cartridge 100. When the magnetic member 24 is at the non-reversing position shown in FIG. 2, the gradient of the magnetic field generated when the electromagnet 22 is turned on is not reversed at the location of the cartridge 100. The non-reversing position is at a distance from the cartridge 100.

The moving actuator 26 includes a motor and other elements, and is capable of moving the magnetic member 24 horizontally and vertically. The moving actuator 26 may move the magnetic member 24 from the reversing position to the non-reversing position, and from the non-reversing position to the reversing position. In the examples of FIGS. 1 and 2, the moving actuator 26 moves the magnetic member 24 horizontally between the reversing position and the non-reversing position. In other words, the reversing position and the non-reversing position are laterally arranged.

The analyzing processor 30 analyzes and processes the image taken by the imager 10. The imager 10 takes an image of the sensor area (sensor area image) at the bottom of the cartridge 100 while the magnetic member 24 is at the non-reversing position shown in FIG. 2. The analyzing processor 30 counts the number of magnetic particles on the sensor area based on the sensor area image to highly sensitively detect the object to be detected contained in the sample. The analyzing processor 30 analyzes the sensor area image to count the number of magnetic particles bonded with the object to be detected that is bonded with the sensor area. The number of magnetic particles relates to the concentration of the object to be detected. That is, as the number of magnetic particles bonded with the sensor area increases, the concentration of the object to be detected increases.

The cartridge 100 is a container set in the sample analyzer 1 when it is analyzed whether the sample contains the object to be detected. The cartridge 100 houses the sample and the magnetic particles that are to be bonded with the object to be detected contained in the sample. In order to analyze whether the sample contains the object to be detected, the cartridge 100 is set to the support frame of the sample analyzer 1. FIGS. 1 and 2 each show the state where the cartridge 100 is set in the sample analyzer 1.

The cartridge 100 has the sensor area at its bottom. A substrate in which the sensor area is formed is an optically transparent substrate formed of such a material as optical glass or quartz glass so that the magnetic particles bonded with the sensor area may be observed or counted by means of the imager 10. On the sensor area, a material, which is, for example, an antibody that may be specifically bonded with the object to be detected through an antigen-antibody reaction, is bonded.

In the first embodiment, when the cartridge 100 is set on the support frame of the sample analyzer 1, the electromagnet 22 is located above (on the first side of) the cartridge 100, and the magnetic member 24 at the reversing position is located below (on the second side of) the cartridge 100. In other words, the reversing position is located between the cartridge 100 and the imager 10 and inserted between the cartridge 100 and the imager 10.

When the magnetic member 24 is at the non-reversing position as shown in FIG. 2, the magnetic member 24 does not prevent the imager 10 from taking an image of the sensor area at the bottom of the cartridge 100. When the magnetic member 24 is at the reversing position as shown in FIG. 1, the magnetic member 24 prevents the imager 10 from taking an image of the sensor area at the bottom of the cartridge 100. Therefore, when the imager 10 takes an image of the sensor area at the bottom of the cartridge 100 in the first embodiment, the magnetic member 24 needs to be moved to the non-reversing position as shown in FIG. 2 by means of the moving actuator 26.

Figure 5:
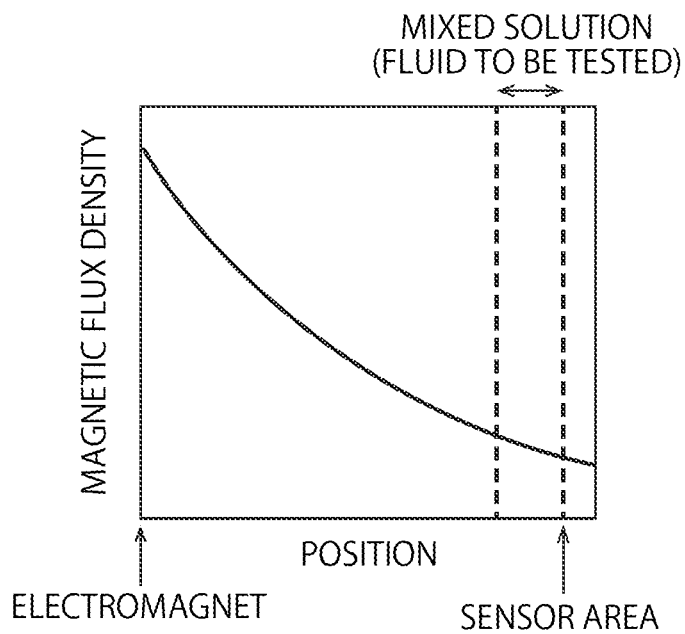
FIG. 5 is a graph showing the change in magnetic flux density of a magnetic field generated by an electromagnet in the first embodiment (when the magnetic member is at a non-reversing position).
Figure 6:
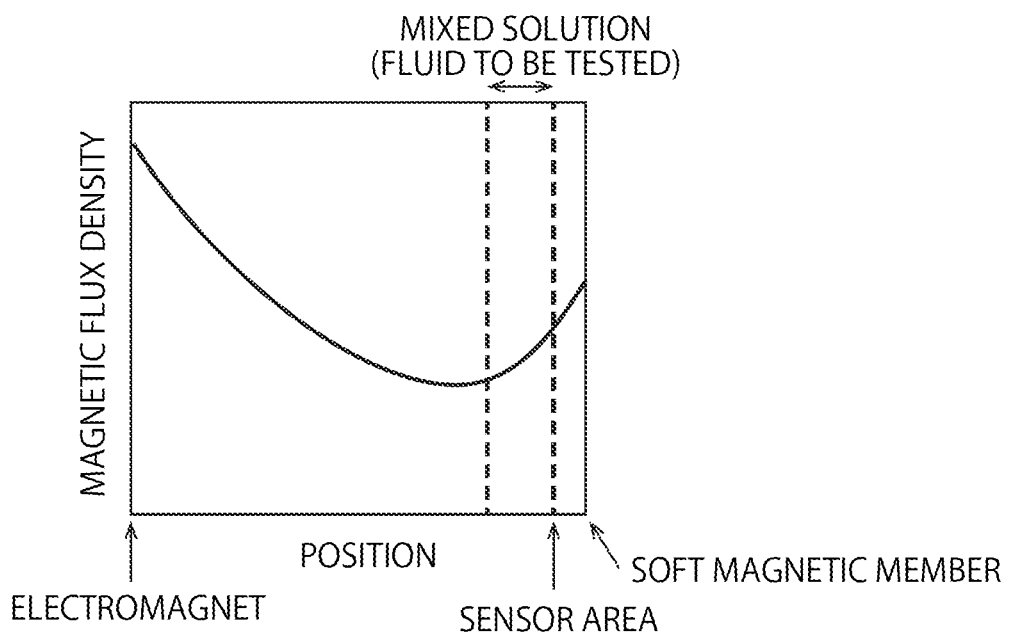
FIG. 6 is a graph showing the change in magnetic flux density of a magnetic field generated by the electromagnet in the first embodiment (when the magnetic member is at a reversing position).

FIGS. 5 and 6 illustrate graphs that show the change in magnetic flux density of the magnetic field generated by the electromagnet 22. More specifically, FIG. 5 shows the change in magnetic flux density when the magnetic member 24 is at the non-reversing position as shown in FIG. 2, and FIG. 6 shows the change in magnetic flux density when the magnetic member 24 is at the reversing position as shown in FIG. 1.

When the magnetic member 24 is at the non-reversing position shown in FIG. 2 and the electromagnet 22 is turned on to generate a magnetic field, the magnetic flux density smoothly decreases from the electromagnet 22 to the cartridge 100 as shown in FIG. 5. As a result, the direction of the magnetic field is changed upward at the location of the cartridge 100 as shown in FIG. 2, and exerts a magnetic power on the magnetic particles housed in the cartridge 100 to move the magnetic particles upward.

When the magnetic member 24 is at the reversing position as shown in FIG. 1, and the electromagnet 22 is turned on to generate a magnetic field, the magnetic flux density decreases as the distance from the electromagnet 22 increases as shown in FIG. 6. Since the magnetic member 24 is magnetized, however, the magnetic flux density increases in an area around the magnetic member 24. As a result, the direction of the magnetic field is downward at the location of the cartridge 100 as shown in FIG. 1, and the magnetic field exerts a magnetic power on the magnetic particles housed in the cartridge 100 to move the magnetic particles downward. In other words, if the cartridge 100 is located in a range in which the magnetic flux density increases as the distance from the electromagnet 22 increases, it is possible to apply a downward magnetic field to the magnetic particles housed in the cartridge 100 to move the magnetic particles downward. Therefore, the magnetic field applier 20 is configured to locate the cartridge 100 in proximity of the magnetic member 24.

The sample analyzer 1 according to the first embodiment uses such a characteristic shown in FIG. 6, and changes the direction of the magnetic field applied from the electromagnet 22 disposed above the cartridge 100 to the magnetic particles housed in the cartridge 100 between upward and downward.

Figure 7:
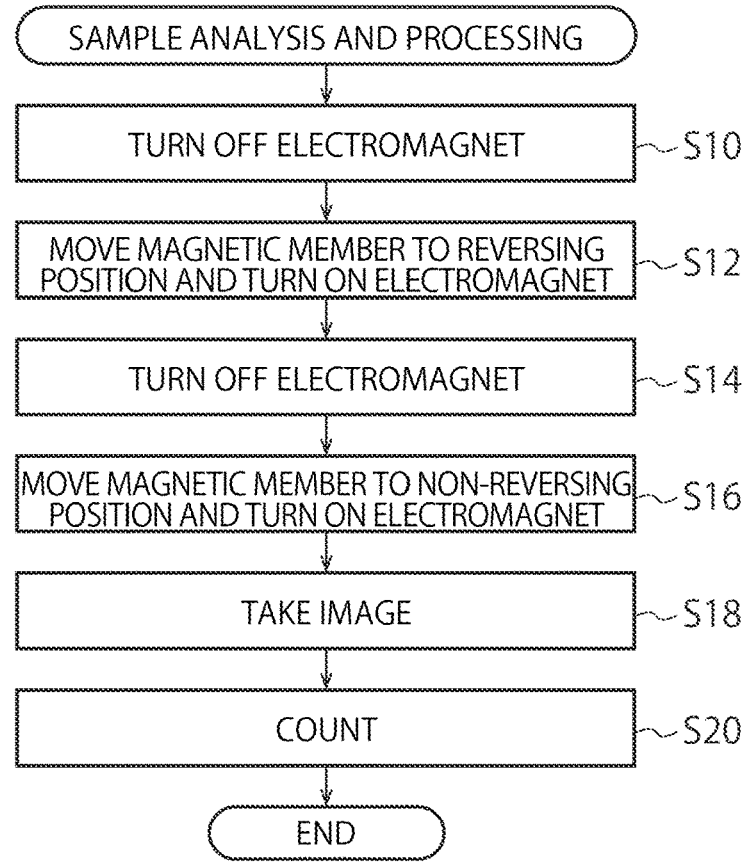
FIG. 7 is a flowchart for explaining an example of a sample analysis operation performed by the sample analyzer according to the first embodiment.
Figure 8:
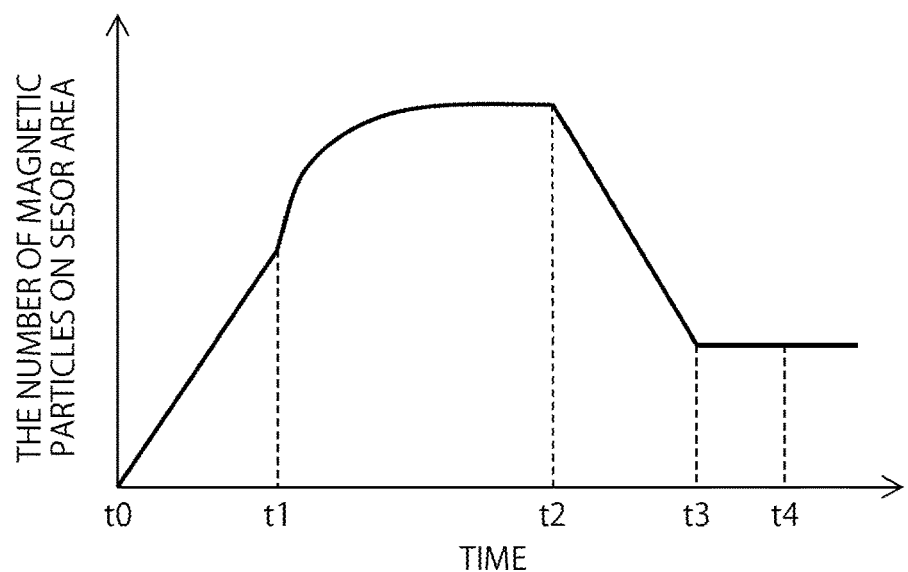
FIG. 8 is a graph showing the change in time of the number of magnetic particles in a sensor area of a cartridge.

The operation of the sample analyzer 1 shown in FIGS. 1 and 2 will then be described with reference to FIGS. 7 and 8. FIG. 7 is a flowchart for explaining a sample analysis operation performed by the sample analyzer 1 according to the first embodiment. FIG. 8 is an example of a graph showing the change in time of the number of magnetic particles on the sensor area of the cartridge 100.

As shown in FIG. 7, the sample analyzer 1 first turns off the electromagnet 22 (step S10). The magnetic member 24 may be set at an arbitrary position, and may be at the reversing position or the non-reversing position. If, however, the magnetic member 24 has a large coercive force and is still greatly magnetized after the electromagnet 22 is turned off, the magnetic member 24 is preferably moved to the non-reversing position.

The user then sets the cartridge 100 at the support frame of the sample analyzer 1, and pours a mixed solution into the cartridge 100, the mixed solution including a sample and magnetic particles that are to be bonded with an object to be detected contained in the sample. The pouring may be automatically or manually performed.

After the mixed solution is poured into the cartridge 100, the sample analyzer 1 moves the magnetic member 24 to the reversing position shown in FIG. 1, and turns on the electromagnet 22 (step S12). The completion of the setting of the cartridge 100 to the sample analyzer 1 may be automatically detected by means of a sensor provided to the sample analyzer 1. Alternatively, the sample analyzer 1 may detect the completion of the setting when the user presses down a setting completion button of the sample analyzer 1.

If the magnetic member 24 is at the reversing position in step S10, the sample analyzer 1 does not need to drive the moving actuator 26 to move the magnetic member 24. However, if the magnetic member 24 is at the non-reversing position, the sample analyzer 1 needs to drive the moving actuator 26 to move the magnetic member 24 from the non-reversing position to the reversing position.

If the electromagnet 22 is turned on when the magnetic member 24 is at the reversing position, the direction of the change in magnetic flux density is reversed at the location of the cartridge 100 as shown in FIG. 6, and a downward magnetic field is applied to the magnetic particles contained in the cartridge 100. In other word, the support frame that holds the cartridge 100 needs to locate the cartridge 100 at a position where the direction of the change in magnetic flux density is reversed as shown in FIG. 6.

When the downward magnetic field is applied to the cartridge 100, the magnetic particles diffusing in the mixed solution poured into the cartridge 100 start precipitating in the mixed solution and reach the sensor area at the bottom of the cartridge 100. During the precipitation, the magnetic particles are bonded with the object to be detected contained in the sample and reach the surface of the sensor area. The precipitation speed of the magnetic particles to which the downward magnetic field is applied is faster than the precipitation speed of the magnetic particles to which only the gravity is applied. In other words, the time required for the precipitation of the magnetic particles may be shortened by applying a downward magnetic field to the cartridge 100. The magnetic particles that are magnetized by the magnetic field adhere to each other by the magnetic power and form a chain-like structure extending upward from the surface of the sensor area.

FIG. 8 illustrates the change in the number of magnetic particles on the sensor area in step S12, from time t0 to time t1. Since the magnetic particles in the mixed solution precipitate, the number of magnetic particles on the sensor area increases as the time passes.

Next, the sample analyzer 1 turns off the electromagnet 22 (step S14). The magnetic member 24 may be located at an arbitrary position, and may be located at the reversing position or the non-reversing position. If, however, the magnetic member 24 has a large coercive force and is still greatly magnetized after the electromagnet 22 is turned off, the magnetic member 24 is preferably moved to the non-reversing position.

In step S14, the magnetic particles are released from the chain-like structure made by the application of the magnetic field, and precipitate due to the gravity. Therefore, the number of magnetic particles on the sensor area increases further. The change in the number of magnetic particles on the sensor area in step S14 is shown from time t1 to time t2 in FIG. 8. The magnetic particles released from the magnetic field precipitate due to the gravity and freely diffuse above the sensor area. Therefore, the number of magnetic particles on the sensor area increases further from time t1 and saturates. If the measurement time needs to be shortened, the time in which the magnetic particles diffuse freely after step S14 may be shortened or omitted after the number of magnetic particles on the sensor area saturates and remains at substantially the same value.

The magnetic particles bonded with the object to be detected and reach and freely diffuse over the sensor area at the bottom of the cartridge 100 are then bonded with the sensor area through the antigen-antibody reaction of the object to be detected with the antibody fixed on the sensor area. The magnetic particles that are not bonded with the object to be detected are not bonded with the antibody fixed on the sensor area. Thus, if the number of magnetic particles bonded with the sensor area is greater, the amount of the object to be detected contained in the sample is greater.

Next, the sample analyzer 1 moves the magnetic member 24 to the non-reversing position shown in FIG. 2, and turns on the electromagnet 22 (step S16). If the magnetic member 24 is at the non-reversing position in step S14, the sample analyzer 1 does not need to drive the moving actuator 26 to move the magnetic member 24. However, if the magnetic member 24 is at the reversing position, the sample analyzer 1 needs to drive the moving actuator 26 to move the magnetic member 24 from the reversing position to the non-reversing position. If the electromagnet 22 is turned on when the magnetic member 24 is at the non-reversing position, the change in magnetic flux density keeps the decrease at the location of the cartridge 100 as shown in FIG. 5. Therefore, an upward magnetic field may be applied to the magnetic particles in the cartridge 100.

When the upward magnetic field is applied to the cartridge 100, the magnetic particles move upward in the mixed solution. However, the magnetic particles bonded with the sensor area due to the antigen-antibody reaction remain on the sensor area against the upward magnetic field. Thus, the magnetic particles bonded with the object to be detected are left on the sensor area.

The change in the number of magnetic particles on the sensor area in step S16 is shown in FIG. 8, from time t2 to time t4. In the period from time t2 to time t3, the magnetic particles that are not bonded with the sensor area are moved up in the mixed solution due to the influence of the upward magnetic field. Therefore, the number of magnetic particles on the sensor area decreases. When all of the magnetic particles that are not bonded with the sensor area are pulled from the sensor area and moved up, the number of magnetic particles on the sensor area does not decrease further. This state is shown in the period after time t3 in FIG. 8.

When a predetermined time has passed after step S16, the sample analyzer 1 takes an image of the sensor area from the lower side of the cartridge 100 by means of the imager 10 (step S18). Since the sensor area is in the optically transparent substrate, the magnetic particles bonded with the sensor area are on the sensor area image taken via the transparent substrate. The image is taken at time t4 in FIG. 8.

The analyzing processor 30 of the sample analyzer 1 then analyzes the sensor area image and counts the number of magnetic particles on the sensor area image (step S20). As the result of the image analysis of the sensor area image, the number of magnetic particles remaining on the sensor area is counted, whether the object to be detected is included in the sample is determined, and the concentration of the object to be detected in the sample is estimated. Then the sample analysis operation of the first embodiment is completed.

As described above, in the sample analyzer 1 according to the first embodiment, the cartridge 100 is set to the sample analyzer 1, the electromagnet 22 is disposed above the cartridge 100, and the magnetic member 24 disposed below the cartridge 100 is moved between the reversing position and the non-reversing position to switch the direction of the magnetic field generated by the electromagnet 22 at the location of the cartridge 100. Therefore, there is no need to dispose an electromagnet below the cartridge 100. This reduces the manufacturing costs of the sample analyzer 1.

Since the imager 10 may be disposed to the position where the electromagnet below the cartridge 100 has been omitted, an image of the sensor area in the cartridge 100 may be taken by the imager 10 from immediately below the cartridge 100.

When the image of the sensor area at the bottom of the cartridge 100 is taken by the imager 10, the magnetic member 24 is moved to the non-reversing position that is laterally away from the reversing position in order not to get in the way of the imager 10. Therefore, the imager 10 may smoothly take an image of the sensor area in the cartridge 100 while the upward magnetic field is applied to the magnetic particles in the mixed solution in the cartridge 100.

Second Embodiment

In the first embodiment described above, the electromagnet 22 is disposed above the cartridge 100, and the imager 10 is disposed below the cartridge 100. On the other hand, in a second embodiment, the imager 10 is disposed above the cartridge 100 and the electromagnet 22 is disposed below the cartridge 100. Differences between the first embodiment and the second embodiment will be described below.

Figure 9:
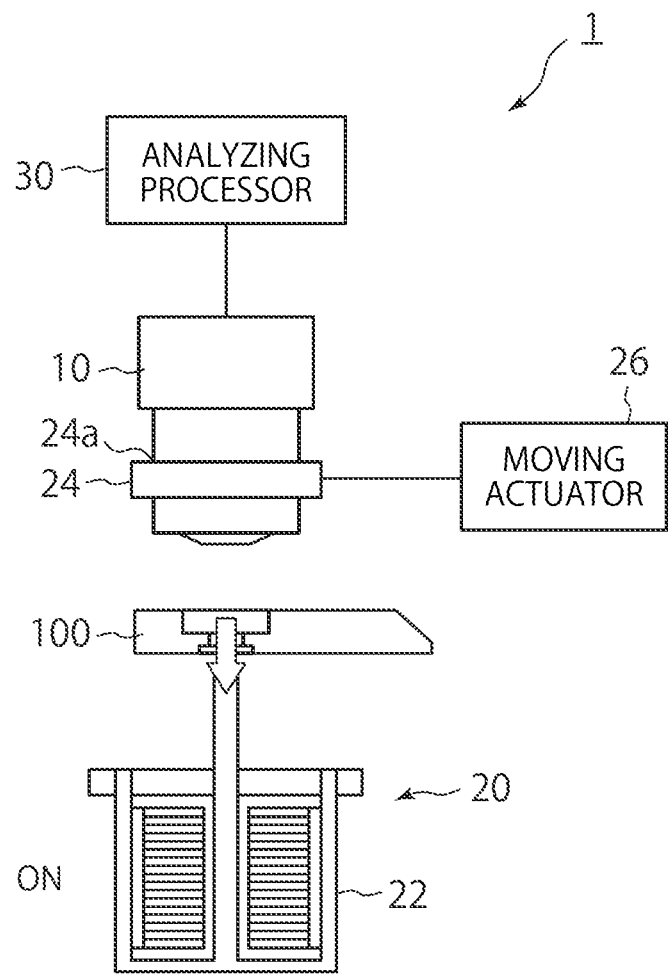
FIG. 9 illustrates a layout of a sample analyzer according to a second embodiment viewed from one side, for explaining the structure of the sample analyzer (a magnetic field is applied to move magnetic particles downward).
Figure 10:
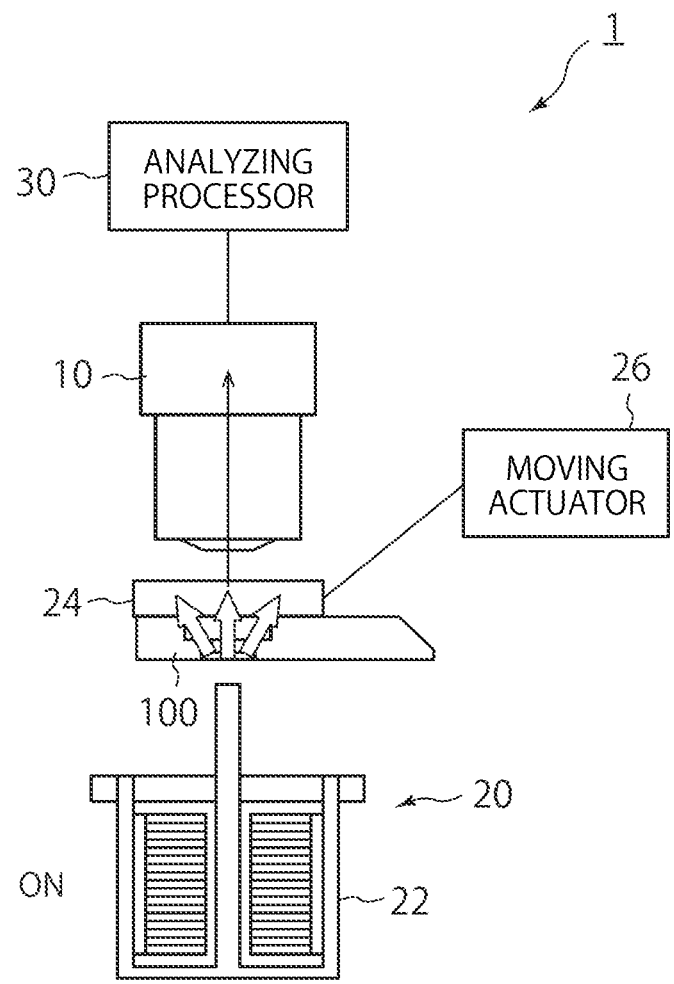
FIG. 10 illustrates a layout of the sample analyzer according to the second embodiment viewed from the one side, for explaining the structure of the sample analyzer (a magnetic field is applied to move magnetic particles upward).

FIGS. 9 and 10 each illustrate a layout of a sample analyzer 1 according to the second embodiment viewed from one side. FIGS. 9 and 10 correspond to FIGS. 1 and 2 of the first embodiment, respectively. FIG. 9 is a layout diagram showing the state in which the sample analyzer 1 moves magnetic particles in a cartridge 100 downward, and a magnetic member 24 is at a non-reversing position for not reversing the gradient of a magnetic field generated by an electromagnet 22. FIG. 10 is a layout diagram showing the state in which the sample analyzer 1 moves the magnetic particles in the cartridge 100 upward, and the magnetic member 24 is at a reversing position for reversing the gradient of the magnetic field generated by the electromagnet 22.

As shown in FIGS. 9 and 10, the sample analyzer 1 according to the second embodiment includes an imager 10, a magnetic field applier 20, and an analyzing processor 30, like the first embodiment described above.

In the second embodiment, however, when the cartridge 100 is set in the sample analyzer 1, the imager 10 is disposed above (on the second side of) the cartridge 100, and the electromagnet 22 included in the magnetic field applier 20 is disposed below (on the first side of) the cartridge 100. The magnetic member 24 included in the magnetic field applier 20 is disposed above the cartridge 100.

Figure 11:
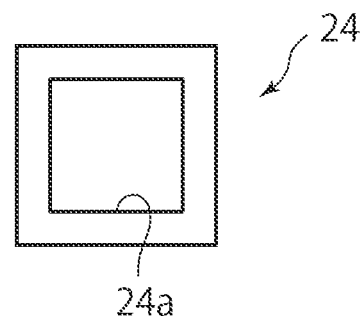
FIG. 11 illustrates a magnetic member included in the sample analyzer according to the second embodiment viewed from above.
Figure 12:
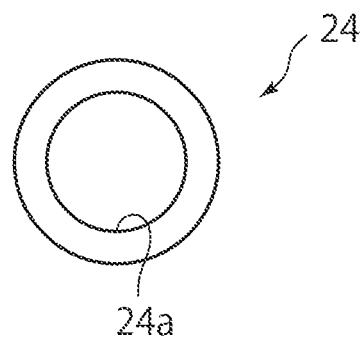
FIG. 12 illustrates another magnetic member included in the sample analyzer according to the second embodiment viewed from above.

In the second embodiment, the magnetic member 24 has a ring-like shape. FIGS. 11 and 12 each show a top view of the magnetic member 24 included in the sample analyzer 1 according to the second embodiment. In the example shown in FIG. 11, the magnetic member 24 has a rectangular shape, and an opening 24a is formed at its central portion. The shape of the opening 24a is also rectangular. In the example of FIG. 12, the magnetic member 24 has a circular shape, and has the opening 24a in the central portion. The shape of the opening 24a is circular. In the second embodiment, when the magnetic member 24 is moved to the non-reversing position, the imager 10 is inserted to the opening 24a of the magnetic member 24. The shapes of the magnetic member 24 and the opening 24a may be arbitrarily determined as long as the imager 10 may be inserted into the opening 24a when the magnetic member 24 is moved from the reversing position to the non-reversing position.

As shown in FIGS. 9 and 10, the moving actuator 26 is capable of moving the magnetic member 24 from the reversing position to the non-reversing position, or vice versa. In the examples shown in FIGS. 9 and 10, the moving actuator 26 moves the magnetic member 24 vertically between the reversing position and the non-reversing position. In other words, the reversing position and the non-reversing position are vertically arranged.

When the magnetic member 24 is moved to the non-reversing position as shown in FIG. 9, the magnetic member 24 is moved away from the cartridge 100 so that the imager 10 may be inserted through the magnetic member 24.

The moving actuator 26 moves the magnetic member 24 upward so that the imager 10 penetrates the opening 24a of the magnetic member 24. On the contrary, the moving actuator 26 moves the magnetic member 24 to the reversing position so that the magnetic member 24 is removed away from the imager 10 and located near the cartridge 100. The moving actuator 26 moves the magnetic member 24 downward until the imager 10 is not in the opening 24a anymore and the magnetic member 24 is placed near the cartridge 100. Thus, the reversing position is located between the cartridge 100 and the imager 10 and inserted between the cartridge 100 and the imager 10.

The upper portion of the cartridge 100 in the second embodiment is formed of an optically transparent substrate, such as an optical glass substrate or a quartz glass substrate so that magnetic particles bonded with the sensor area may be observed or counted from above. The sensor area is formed on the bottom of the cartridge 100, and a material that may be specifically bonded with an object to be detected through an antigen-antibody reaction, for example an antibody, is bonded with the sensor area, like the first embodiment.

Figure 13:
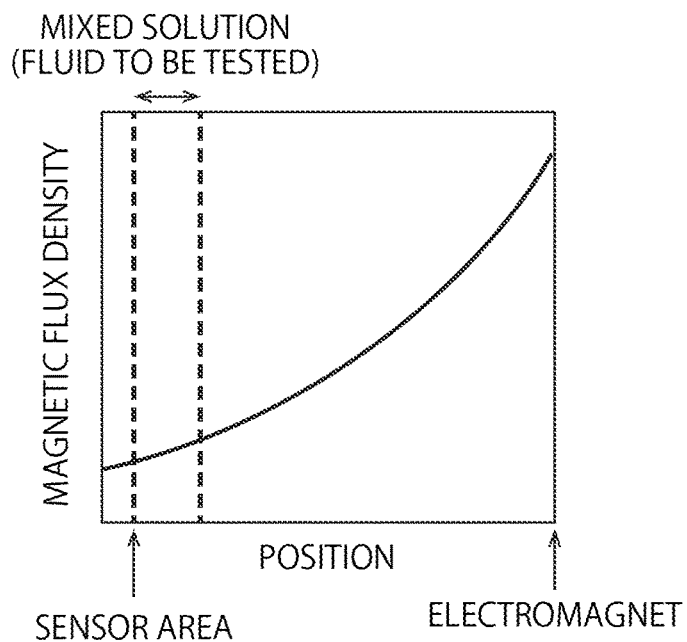
FIG. 13 is a graph showing the change in magnetic flux density of a magnetic field generated by an electromagnet in the second embodiment (when the magnetic member is at a non-reversing position).
Figure 14:
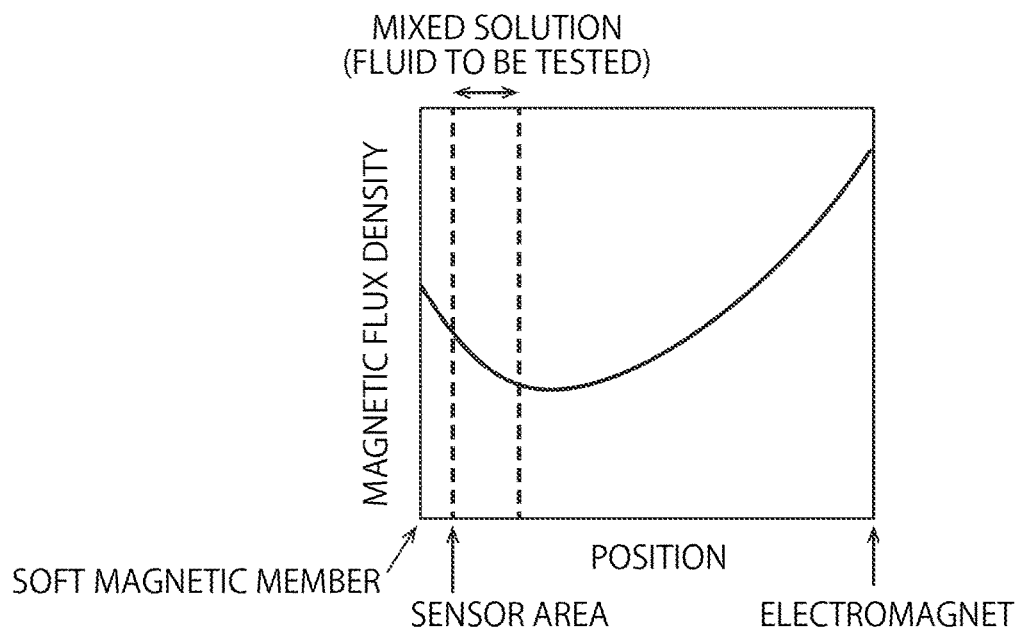
FIG. 14 is a graph showing the change in magnetic flux density of a magnetic field generated by the electromagnet in the second embodiment (when the magnetic member is at a reversing position).

FIGS. 13 and 14 illustrate graphs that show the change in magnetic flux density of the magnetic field generated by the electromagnet 22 in the sample analyzer 1 according to the second embodiment. FIGS. 13 and 14 correspond to FIGS. 5 and 6 of the first embodiment, respectively. More specifically, FIG. 13 shows the change in magnetic flux density when the magnetic member 24 is at the non-reversing position shown in FIG. 9, and FIG. 14 shows the change in magnetic flux density when the magnetic member 24 is at the reversing position shown in FIG. 10.

As shown in FIG. 13, when the magnetic member 24 is at the non-reversing position as shown in FIG. 9 and the electromagnet 22 is turned on to generate a magnetic field, the magnetic flux density smoothly decreases from the electromagnet 22 to the cartridge 100. As a result, the direction of the magnetic field is downward at the location of the cartridge 100 as shown in FIG. 9, and exerts a magnetic power on the magnetic particles housed in the cartridge 100 to move the magnetic particles downward.

When the magnetic member 24 is at the reversing position shown in FIG. 10 and the electromagnet 22 is turned on to generate a magnetic field, the magnetic flux density decreases as the distance from the electromagnet 22 increases as shown in FIG. 14. Since the magnetic member 24 is magnetized, however, the magnetic flux density increases in an area around the magnetic member 24. As a result, the direction of the magnetic field is upward at the location of the cartridge 100 as shown in FIG. 10, and the magnetic field exerts a magnetic power on the magnetic particles housed in the cartridge 100 to move the magnetic particles upward. In other words, if the cartridge 100 is located in a range in which the magnetic flux density increases as the distance from the electromagnet 22 increases, it is possible to apply an upward magnetic field to the magnetic particles housed in the cartridge 100 to move the magnetic particles upward.

The operation of the sample analyzer 1 shown in FIGS. 9 and 10 will then be described with reference to FIG. 15, which is a flowchart for explaining a sample analysis operation performed by the sample analyzer 1 according to the second embodiment. The change in time of the number of magnetic particles on the sensor area of the cartridge 100 is the same as that in the first embodiment shown in FIG. 8. Therefore, if necessary, FIG. 8 will be referred to.

Figure 15:
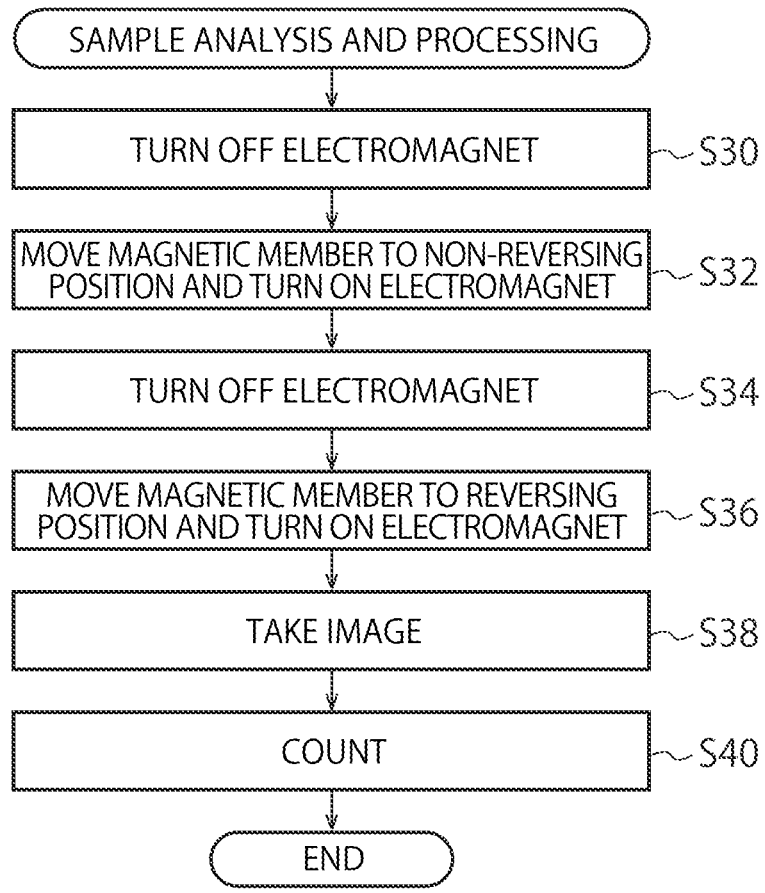
FIG. 15 is a flowchart for explaining an example of a sample analysis operation performed by the sample analyzer according to the second embodiment.

As shown in FIG. 15, the sample analyzer 1 turns off the electromagnet 22 (step S30). Step S30 is performed in the same manner as step S10 in the first embodiment. The magnetic member 24 may be at an arbitrary position, and may be at the reversing position or the non-reversing position. If, however, the magnetic member 24 has a large coercive force and is still greatly magnetized after the electromagnet 22 is turned off, the magnetic member 24 is preferably moved to the non-reversing position.

The user then sets the cartridge 100 at the support frame of the sample analyzer 1, and pours a mixed solution into the cartridge 100, the mixed solution including a sample and magnetic particles that are to be bonded with an object to be detected contained in the sample. The pouring may be automatically or manually performed.

After the mixed solution is poured into the cartridge 100, the sample analyzer 1 moves the magnetic member 24 to the non-reversing position shown in FIG. 9, and turns on the electromagnet 22 (step S32). As in the first embodiment described above, the completion of the setting of the cartridge 100 to the sample analyzer 1 may be automatically detected by means of a sensor provided to the sample analyzer 1. Alternatively, the sample analyzer 1 may detect the completion of the setting when the user presses down a setting completion button of the sample analyzer 1.

If the magnetic member 24 is at the non-reversing position at step S30, the sample analyzer 1 does not need to drive the moving actuator 26 to move the magnetic member 24. However, if the magnetic member 24 is at the reversing position, the sample analyzer 1 drives the moving actuator 26 to move the magnetic member 24 from the reversing position to the non-reversing position.

If the electromagnet 22 is turned on when the magnetic member 24 is at the non-reversing position, it is possible to apply a downward magnetic field to the magnetic particles in the cartridge 100 as shown in FIG. 9.

When the downward magnetic field is applied to the cartridge 100, the magnetic particles diffusing in the mixed solution poured into the cartridge 100 start precipitating in the mixed solution and enter the sensor area at the bottom of the cartridge 100. During the precipitation, the magnetic particles are bonded with the object to be detected contained in the sample. The precipitation speed of the magnetic particles to which the downward magnetic field is applied is faster than the precipitation speed of the magnetic particles to which only the gravity is applied. In other words, the time required for the precipitation of the magnetic particles may be shortened by applying a downward magnetic field to the cartridge 100. The magnetic particles that are magnetized by the magnetic field adhere to each other by the magnetic power and form a chain-like structure extending upward from the surface of the sensor area.

FIG. 8 illustrates the change in the number of magnetic particles on the sensor area in step S32, from time t0 to time t1. Since the magnetic particles in the mixed solution precipitates, the number of magnetic particles on the sensor area increases as the time passes.

Next, the sample analyzer 1 turns off the electromagnet 22 (step S34). The magnetic member 24 may be located at an arbitrary position, and may be located at the reversing position or the non-reversing position. If, however, the magnetic member 24 has a large coercive force and is still greatly magnetized after the electromagnet 22 is turned off, the magnetic member 24 is preferably not moved from the non-reversing position.

In step S34, the magnetic particles are released from the chain-like structure made by the application of the magnetic field, and precipitate due to the gravity. Therefore, the number of magnetic particles on the sensor area increases further. The change in the number of magnetic particles on the sensor area in step S34 is shown from time t1 to time t2 in FIG. 8. The magnetic particles released from the magnetic field precipitate due to the gravity and freely diffuse above the sensor area. Therefore, the number of magnetic particles on the sensor area increases further from time t1 and saturates. If the measurement time needs to be shortened, the time in which the magnetic particles diffuse freely after step S34 may be shortened or omitted after the number of magnetic particles on the sensor area saturates and remains at substantially the same value.

The magnetic particles bonded with the object to be detected and reach and freely diffuse over the sensor area at the bottom of the cartridge 100 are bonded with the sensor area through the antigen-antibody reaction of the object to be detected with the antibody fixed on the sensor area. The magnetic particles that are not bonded with the object to be detected are not bonded with the antibody fixed on the sensor area. Thus, if the number of magnetic particles bonded with the sensor area is greater, the amount of the object to be detected contained in the sample is greater.

Next, the sample analyzer 1 moves the magnetic member 24 to the reversing position shown in FIG. 10, and turns on the electromagnet 22 (step S36). If the magnetic member 24 has already been moved to the reversing position in step S34, the sample analyzer 1 does not need to drive the moving actuator 26 to move the magnetic member 24. However, if the magnetic member 24 is at the non-reversing position, the sample analyzer 1 needs to drive the moving actuator 26 to move the magnetic member 24 from the non-reversing position to the reversing position. If the electromagnet 22 is turned on when the magnetic member 24 is at the reversing position, the gradient of the magnetic field may be reversed at the cartridge 100 as shown in FIG. 10. Therefore, an upward magnetic field may be applied to the magnetic particles in the cartridge 100.

When the upward magnetic field is applied to the cartridge 100, the magnetic particles move upward in the mixed solution. However, the magnetic particles bonded with the sensor area due to the antigen-antibody reaction remain on the sensor area against the upward magnetic field. Thus, the magnetic particles bonded with the object to be detected are left on the sensor area.

The change in the number of magnetic particles on the sensor area in step S36 is shown in FIG. 8, from time t2 to time t4. In the period from time t2 to time t3, the magnetic particles that are not bonded with the sensor area are moved up in the mixed solution due to the influence of the upward magnetic field. Therefore, the number of magnetic particles on the sensor area decreases. When all of the magnetic particles that are not bonded with the sensor area are pulled from the sensor area and moved up, the number of magnetic particles on the sensor area does not decrease further. This state is shown in the period after time t3 in FIG. 8.

When a predetermined time has passed after step S36, the sample analyzer 1 takes an image of the sensor area from above the cartridge 100 by means of the imager 10 (step S38). Since the upper portion of the cartridge 100 is formed of an optically transparent substrate, the magnetic particles bonded with the sensor area are on the sensor area image taken via the transparent substrate. The image is taken at time t4 in FIG. 8.

Figure 16:
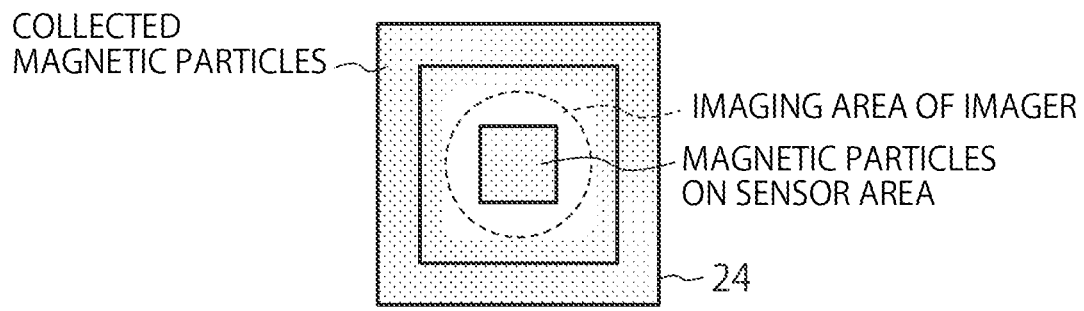
FIG. 16 illustrates an example of the positional relationship among an sensor area, an imaging area of the imager, and a magnetic member.

FIG. 16 illustrates an example of the positional relationship among the sensor area, the imaging area of the imager, and the magnetic member. As shown in FIG. 16, when the magnetic member 24 is at the reversing position, the magnetic particles in the mixed solution are attracted to the magnetic member 24. Therefore, the magnetic particles collect along the magnetic member 24 having the ring-like shape. As the result, no magnetic particles are left in the opening 24a of the magnetic member 24, which allows the sensor area to be viewed from above the cartridge 100 through the transparent substrate on the upper portion of the cartridge 100. More specifically, the magnetic particles that are moved toward the upper portion of the mixed solution due to the magnetic force of the upper magnetic field are attracted to the ring-like magnetic member 24 having the magnetic power, leaving no magnetic particles in the opening 24a. In the second embodiment, the image of the sensor area in the cartridge 100 is taken through the opening 24a from which the magnetic particles are removed.

Next, the analyzing processor 30 of the sample analyzer 1 analyzes the sensor area image and counts the number of magnetic particles on the sensor area image (step S40). More specifically, the analyzing processor 30 performs image analysis of the sensor area image to count the number of magnetic particles on the sensor area, determine whether the sample contains the object to be detected, and estimate the concentration of the object to be detected in the sample. The sample analysis operation of the second embodiment is then completed.

As described above, in the sample analyzer 1 according to the second embodiment, the cartridge 100 is set to the sample analyzer 1, the imager 10 is disposed above the cartridge 100, and the magnetic member 24 disposed below the cartridge 100 is moved between the reversing position and the non-reversing position to switch the direction of the magnetic field generated by the electromagnet 22 at the location of the cartridge 100. Therefore, there is no need to dispose an electromagnet above the cartridge 100. This reduces the manufacturing costs of the sample analyzer 1.

Since the imager 10 may be disposed to the position where the electromagnet above the cartridge 100 has been omitted, an image of the sensor area in the cartridge 100 may be taken by the imager 10 from immediately above the cartridge 100.

Furthermore it is possible to take an image of the sensor area of the cartridge 100 by means of the imager 10 through the opening 24a of the magnetic member 24 and through the transparent substrate at the upper portion of the cartridge 100, because the magnetic member 24 has a ring-like shape so as not to get in the way of the imager 10.

Moreover, the moving actuator 26 of the second embodiment may be configured to move the magnetic member 24 not only vertically but also horizontally. More specifically, in the state shown in FIG. 10, the moving actuator 26 may move the magnetic member 24 also in the horizontal direction so that the magnetic member 24 is laterally away from the sensor area of the cartridge 100. In this case, the magnetic particles drawn upward in the cartridge 100 may horizontally move in the mixed solution in the cartridge 100 along with moving the magnetic member 24 horizontally, and then the magnetic particles may move to a location at which the magnetic particles do not get in the way of the imager 10.

Figure 17:
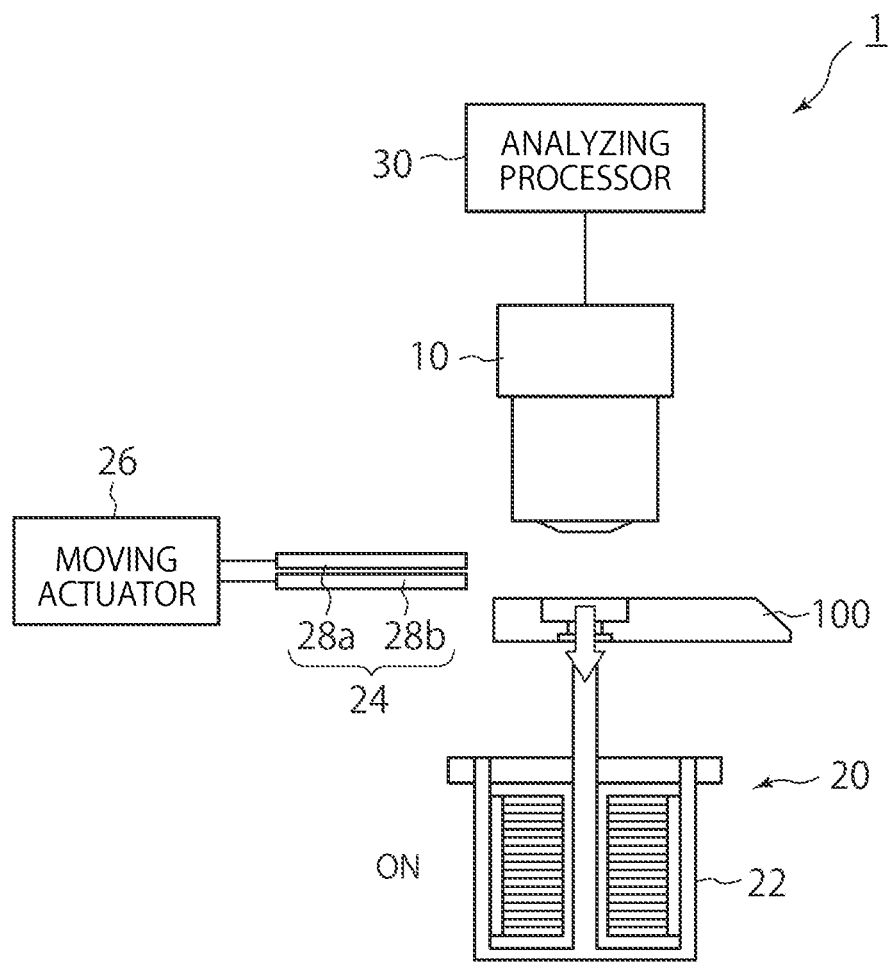
FIG. 17 illustrates a layout of a sample analyzer according to a modification of the second embodiment viewed from one side, for explaining the structure of the sample analyzer (a magnetic field is applied to move magnetic particles downward).
Figure 18:
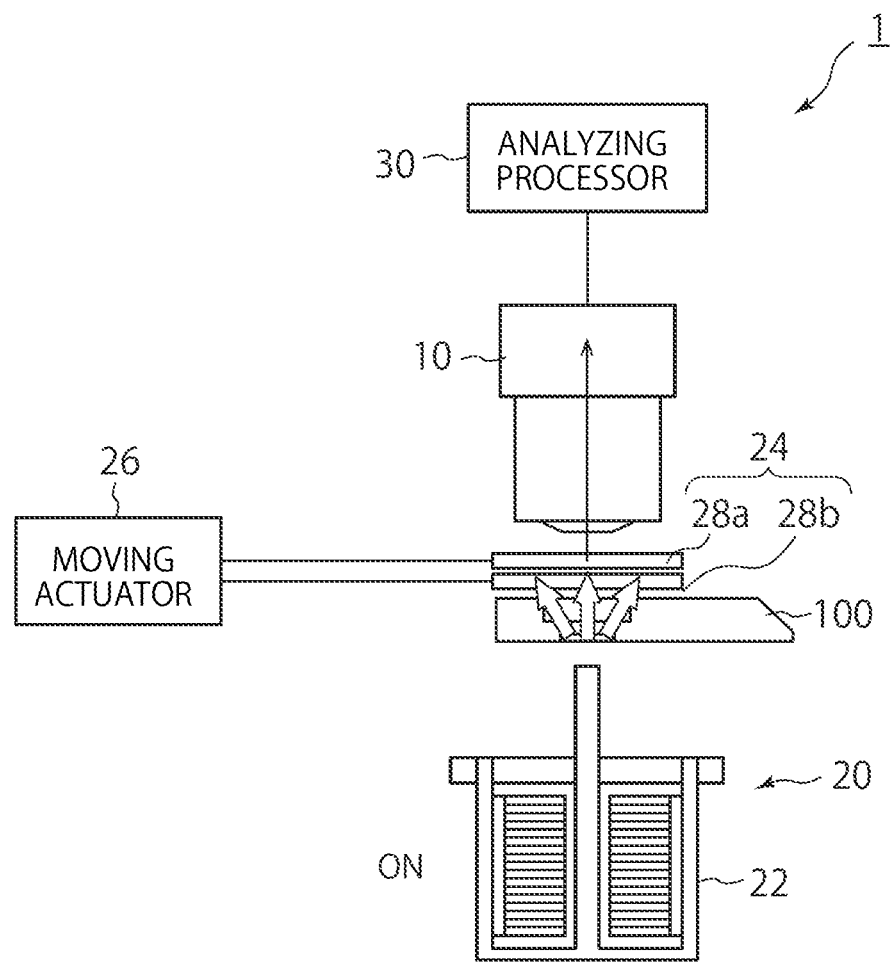
FIG. 18 illustrates a layout of the sample analyzer according to the modification of the second embodiment viewed from the one side, for explaining the structure of the sample analyzer (in a first state in which a magnetic field is applied to move magnetic particles upward).
Figure 19:
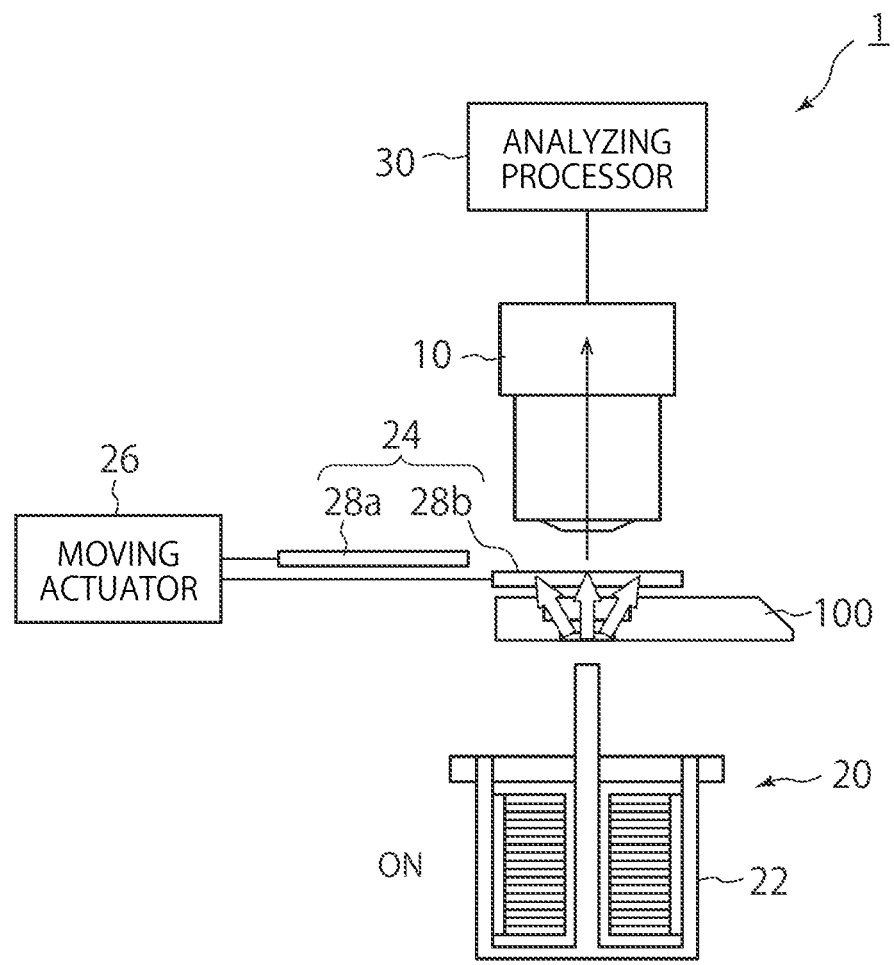
FIG. 19 illustrates a layout of the sample analyzer according to the modification of the second embodiment viewed from the one side, for explaining the structure of the sample analyzer (in a second state in which a magnetic field is applied to move magnetic particles upward).

The magnetic member 24 may include a plurality of magnetic members as shown in FIGS. 17 to 19. In the examples shown in FIGS. 17 to 19, the magnetic member 24 includes two magnetic members, a first magnetic member 28a and a second magnetic member 28b. The first magnetic member 28a has a flat plate shape in the same manner as the first embodiment, and the second magnetic member 28b has a ring-like shape in the same manner as the second embodiment.

When the magnetic member 24 is at the non-reversing position as shown in FIG. 17, both the first magnetic member 28a and the second magnetic member 28b have been horizontally moved from the reversing position and at a location away from the cartridge 100. Therefore, even if the electromagnet 22 is turned on, the direction of the gradient of the magnetic field generated by the electromagnet 22 is not reversed.

In order to reverse the direction of the gradient of the magnetic field generated by the electromagnet 22, the moving actuator 26 firstly moves the magnetic member 24 to the reversing position shown in FIG. 18. Specifically, both the first magnetic member 28a and the second magnetic member 28b are moved to the reversing position between the imager 10 and the cartridge 100. The two magnetic members 28a and 28b reverse the direction of the gradient of the magnetic field, and the upward magnetic field may be applied to the magnetic particles in the mixed solution contained in the cartridge 100.

After a predetermined time passes and the magnetic particles collect to an upper portion of the mixed solution, the moving actuator 26 moves the first magnetic member 28a to the non-reversing position and leaves the second magnetic member 28b at the reversing position, as shown in FIG. 19. In the state shown in FIG. 19, the magnetic particles having been drawn to the upper portion of the mixed solution are attracted by the ring-like second magnetic member 28b, and no magnetic particles except for those bonded with the sensor area are left in an area of an opening formed in the second magnetic member 28b. The state of the magnetic particles is shown in FIG. 16. Therefore, the magnetic particles drawn to the upper portion of the mixed solution do not get in the way of the imager 10 when the imager 10 takes an image of the sensor area from above the cartridge 100.

The vertical positions of the first magnetic member 28a and the second magnetic member 28b may be reversed. Specifically, the first magnetic member 28a having a flat plate shape may be disposed below, and the second magnetic member 28b having a ring-like shape may be disposed above.

Figure 20:
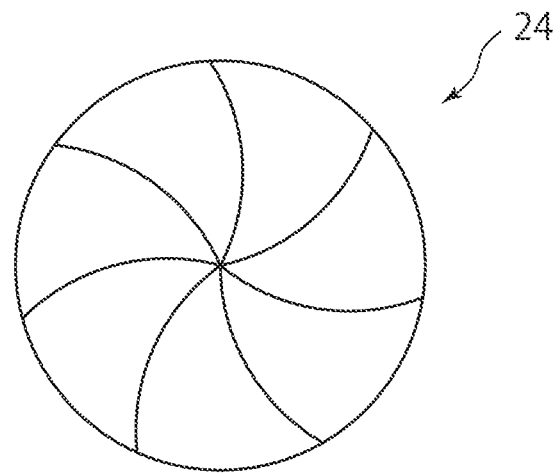
FIG. 20 is a plan view of a magnetic member of a sample analyzer according to a further modification of the second embodiment viewed from above (an iris diaphragm is closed).
Figure 21:
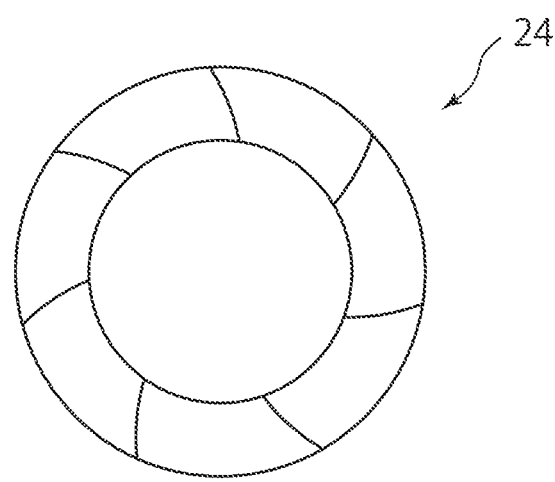
FIG. 21 is a plan view of the magnetic member of the sample analyzer according to the further modification of the second embodiment (the iris diaphragm is opened).

Moreover, the magnetic member 24 may have a shape like an iris diaphragm as shown in FIGS. 20 and 21. FIG. 20 is a top view of the magnetic member 24 in which the iris diaphragm is closed, and FIG. 21 is a top view of the magnetic member 24 in which the iris diaphragm is opened.

In order to set the magnetic member 24 at the reversing position, the magnetic member 24 is inserted between the imager 10 and the cartridge 100 as shown in FIG. 10 or FIG. 18. When an upper magnetic field is applied to the magnetic particles in the mixed solution contained in the cartridge 100, the iris diaphragm of the magnetic member 24 is closed as shown in FIG. 20 to attract the magnetic particles in the mixed solution to the upper portion.

After a predetermined time passes and the magnetic particles collect to an upper portion of the mixed solution, the iris diaphragm of the magnetic member 24 is opened as shown in FIG. 21. As the result, the magnetic particles in the upper portion of the mixed solution are attracted to the magnetic member 24 along the shape of the magnetic member 24, and no magnetic particles except for those bonded with the sensor area are left in an area of an opening formed by opening the iris diaphragm. The state of the magnetic particles is shown in FIG. 16. Therefore, the magnetic particles drawn to the upper portion of the mixed solution do not get in the way of the imager 10 when the imager 10 takes an image of the sensor area from above the cartridge 100.

Incidentally, in the examples shown in FIGS. 20 and 21, in order to set the magnetic member 24 at the non-reversing position, the magnetic member 24 may be moved upward with the iris diaphragm being open so that the imager 10 may penetrate the opening formed by opening the iris diaphragm as shown in FIG. 9, or moved horizontally to be away from the cartridge 100 as shown in FIG. 17.

Third Embodiment

Although the measurer to measure the magnetic particles in the cartridge 100 is composed of the imager 10 in the first embodiment and the second embodiment explained above, the measurer is not limited to the imager 10. For example, the measurer may be composed of an optical measurer such that a light from the optical measurer is incident on the cartridge 100 and the light emitted from the cartridge 100 is received by the optical measurer. Hereinafter, a third embodiment will be explained in a case where the imager 10 is replaced with the optical measurer in the first embodiment and the second embodiment.

Figure 22:
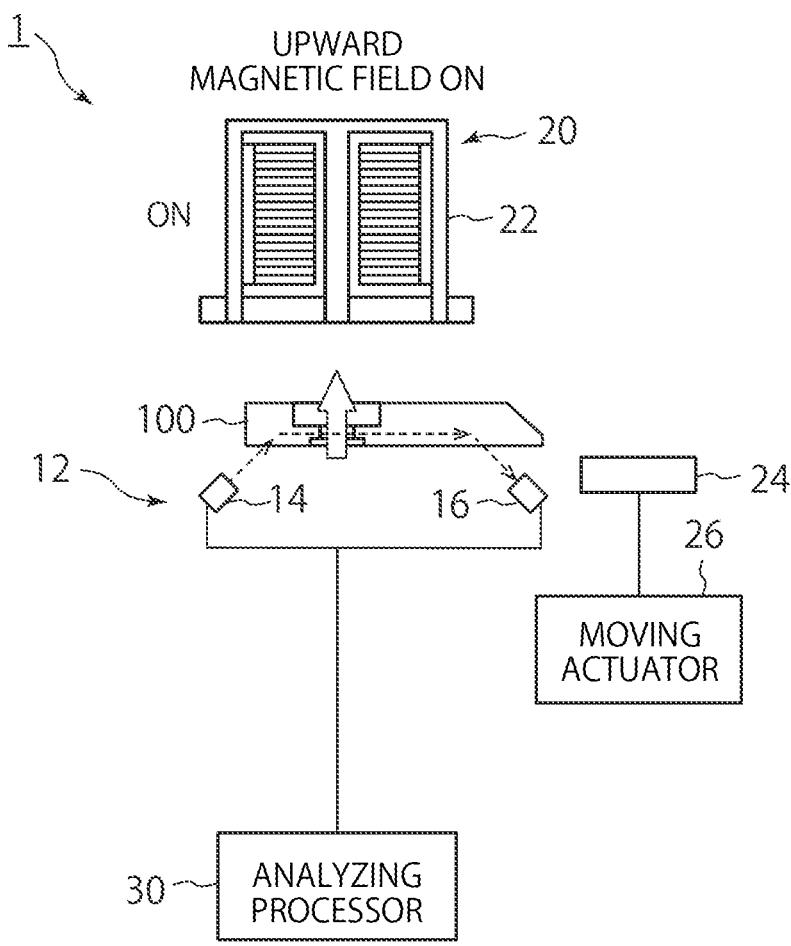
FIG. 22 illustrates a layout of a sample analyzer according to a third embodiment viewed from a one side, for explaining the structure of the sample analyzer (an example of a modification of the first embodiment).
Figure 23:
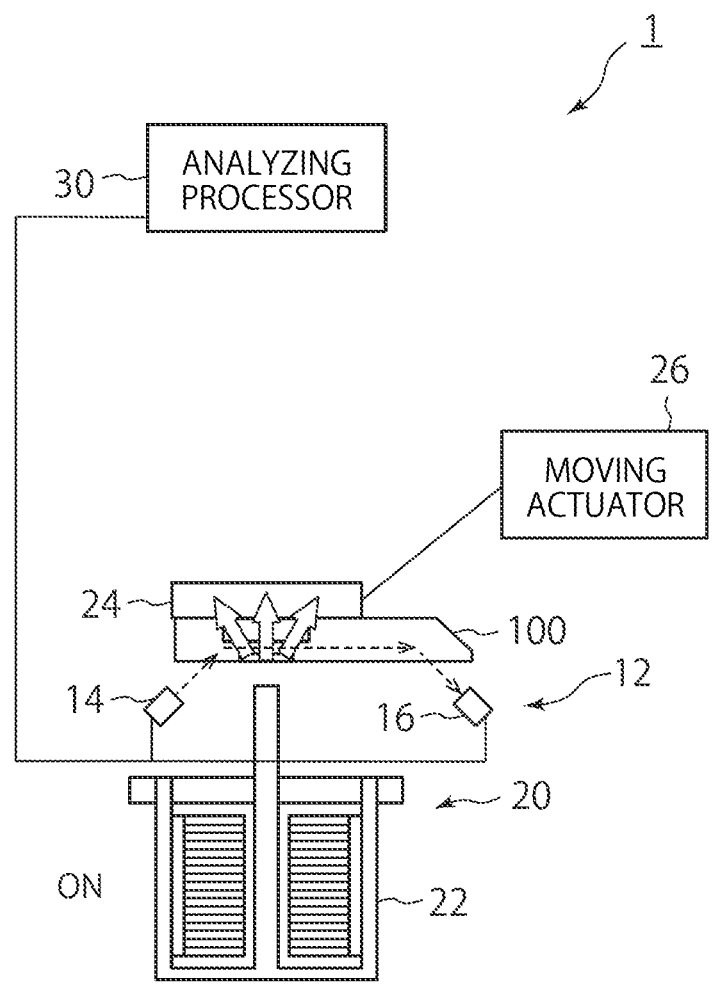
FIG. 23 illustrates a layout of a sample analyzer according to the third embodiment viewed from the one side, for explaining another structure of the sample analyzer (an example of a modification of the second embodiment).

FIG. 22 illustrates a layout of a sample analyzer 1 in which the imager 10 is replaced with an optical measurer 12 in the first embodiment mentioned above, and it corresponds to FIG. 2 of the first embodiment. FIG. 23 illustrates a layout of a sample analyzer 1 in which imager 10 is replaced with an optical measurer 12 in the second embodiment, and it corresponds to FIG. 10 of the second embodiment.

In FIGS. 22 and 23, the optical measurer 12 includes a light source 14 and a light receiver 16. The light source 14 generates a light incident on the cartridge 100. The light incident on the cartridge 100 from an incident side grating of the cartridge 100 is propagated through a wave guide in the cartridge 100 and emitted from an emission side grating of the cartridge 100. The emitted light is received by the light receiver 16.

The analyzing processor 30 calculates a light absorption factor based on a light intensity incident on the cartridge 100 and a light intensity emitted from the cartridge 100. The analyzing processor 30 decides an amount of the magnetic particles bonded with the sensor area of the cartridge 100, and calculates a concentration of the object to be detected.

When the optical measurer 12 measures the amount of the magnetic particles bonded with the sensor area of the cartridge 100, the upward magnetic field is applied to the cartridge 100 as shown in FIGS. 22 and 23. As a result, although the magnetic particles bonded with the sensor area due to the antigen-antibody reaction remain on the sensor area, the other magnetic particles move upward in the mixed solution. In this way, even by using the optical measurer 12, it is possible to measure the magnetic particles bonded with the sensor area.

Furthermore, in the sample analyzer 1 shown in FIG. 23, since the magnetic member 24 does not get in the way of the optical measurer 12 to measure the magnetic particles, a shape of the magnetic member 24 may be arbitrarily selected. That is, in the second embodiment explained above, the magnetic member 24 has an opening as shown in FIGS. 11 and 12. On the other hand, in the third embodiment, since the optical measurer 12 is located below the sensor area of the cartridge 100, the existence of the magnetic member 24 does not obstruct the measurement of the magnetic particles by the optical measurer 12. Therefore, the freedom of design of the magnetic member 24 is increased.

Figure 24:
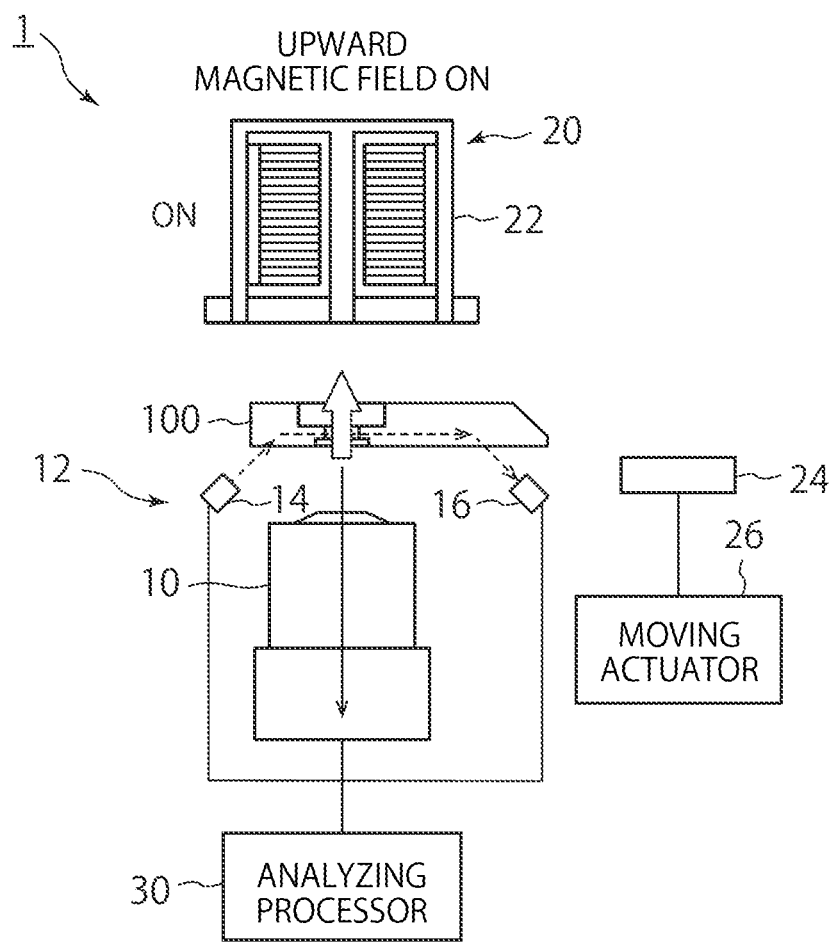
FIG. 24 illustrates a layout of a sample analyzer according to a third embodiment viewed from the one side, for explaining still another structure of the sample analyzer (an example of a modification of the first embodiment).

Incidentally, in the sample analyzer 1 according to the present embodiment, both the imager 10 and the optical measurer 12 may be provided as the measurer. More specifically, as shown in FIG. 24, the optical measurer 12 may be provided in addition to the imager 10 in the first embodiment. Also, as shown in FIG. 25, the optical measurer 12 may be provided in addition to the imager 10 in the second embodiment.

Figure 25:
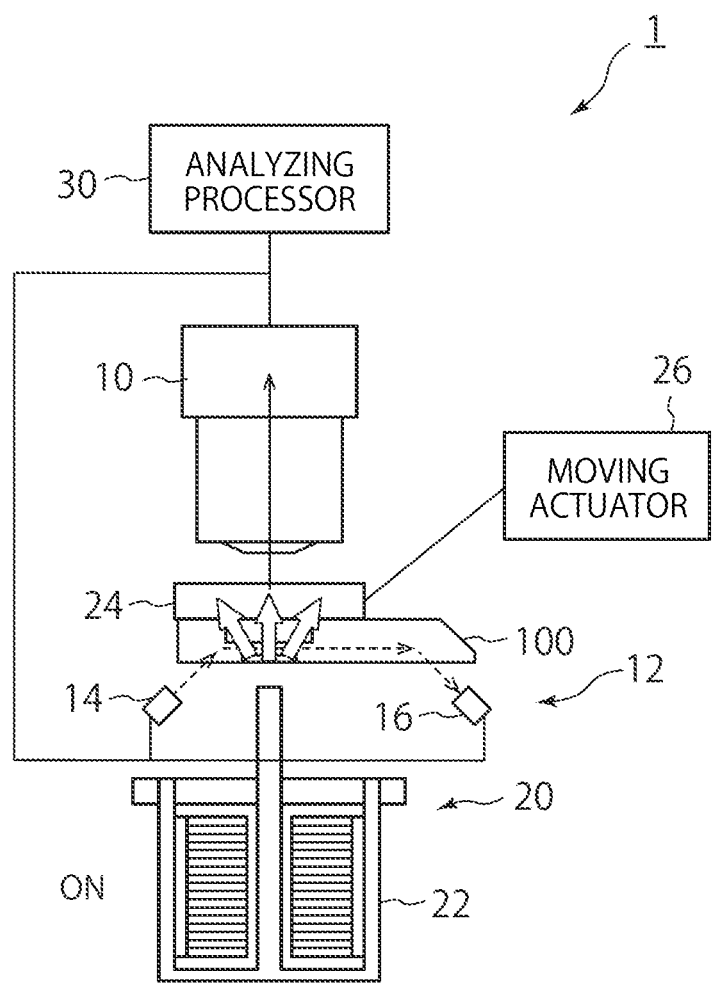
FIG. 25 illustrates a layout of a sample analyzer according to the third embodiment viewed from the one side, for explaining still another structure of the sample analyzer (an example of a modification of the second embodiment).

In the sample analyzer 1 shown in FIGS. 24 and 25, it is arbitrarily selected to measure the magnetic particles in the cartridge 100 either with the imager 10 or with the optical measurer 12. In addition, it is also arbitrarily selected to calculate the amount of the magnetic particles based the measurement result either of the imager 10 or of the optical measurement 12.

For example, both the image 10 and the optical measurer 12 measure the magnetic particles in the cartridge 100, and then the amount of the magnetic particles may be calculated based on the measurement result of the image 10 if the amount of the magnetic particles bonded with the sensor area of the cartridge 100 is few (for example, equal to or fewer than a threshold) whereas the amount of the magnetic particles may be calculated based on the measurement result of the optical measurer 12 if the amount of the magnetic particles bonded with the sensor area of the cartridge 100 is many (for example, more than the threshold). In this way, the amount of the magnetic particles can be measured in a high accuracy even if the amount of the magnetic particles bonded with the sensor area of the cartridge 100 is few or many. That is, the sample analyzer 1 with a wide range of the measurement can be implemented.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A sample analyzer, comprising:
a magnetic field applier configured to apply a magnetic field to a cartridge containing a sample and magnetic particles that bond an object to be detected in the sample;
a measurer configured to measure the magnetic particles in the cartridge; and
an analyzing processor configured to analyze and process a result of a measurement by the measurer,
the magnetic field applier comprising:
an electromagnet disposed on a first side of the cartridge;
a magnetic member configured to be magnetized by the electromagnet; and
a moving actuator configured to move the magnetic member.

2. The sample analyzer according to claim 1, wherein the magnetic member is disposed on a second side of the cartridge, the second side being opposite to the first side.

3. The sample analyzer according to claim 1, wherein a moving direction of the magnetic particles in the cartridge is changed by moving the magnetic member by the moving actuator.

4. The sample analyzer according to claim 2, wherein the moving actuator is further configured to move the magnetic member between a reversing position and a non-reversing position,
a direction of a gradient of a magnetic field generated by the electromagnet is reversed at a location of the cartridge when the magnetic member is at the reversing position, and
the direction of the gradient of the magnetic field generated by the electromagnet is not reversed at the location of the cartridge when the magnetic member is at the non-reversing position.

5. The sample analyzer according to claim 4, wherein the measurer is an imager configured to take an image of the cartridge; and
the analyzing processor is further configured to analyze and process the image taken by the imager.

6. The sample analyzer according to claim 5, wherein:
the first side of the cartridge where the electromagnet is disposed is an upper side of the cartridge, and the second side of the cartridge where the magnetic member is disposed is a lower side of the cartridge; and the reversing position is located between the cartridge and the imager and inserted between the cartridge and the imager.

7. The sample analyzer according to claim 6, wherein the magnetic member has a flat plate shape.

8. The sample analyzer according to claim 6, wherein the non-reversing position and the reversing position are laterally arranged, and at the non-reversing position, the magnetic member does not get in the way of the imager when the imager takes the image of the cartridge.

9. The sample analyzer according to claim 5, wherein:
the first side of the cartridge where the electromagnet is disposed is a lower side of the cartridge, and the second side of the cartridge where the magnetic member is disposed is an upper side of the cartridge; and
the reversing position is located between the cartridge and the imager and inserted between the cartridge and the imager.

10. The sample analyzer according to claim 9, wherein the magnetic member has a ring shape.

11. The sample analyzer according to claim 10, wherein the non-reversing position is above the reversing position, and when the magnetic member is at the non-reversing position, the imager is inserted into an opening formed in the magnetic member.

12. The sample analyzer according to claim 9, wherein:
the magnetic member includes a first magnetic member having a flat plate shape, and a second magnetic member having a ring shape; and
the first magnetic member and the second magnetic member at the reversing position move the magnetic particles upward when the magnetic member is at the reversing position, and then the first magnetic member is moved to the non-reversing position.

13. The sample analyzer according to claim 9, wherein:
the magnetic member has an iris diaphragm shape; and
the iris diaphragm of the magnetic member is closed to move the magnetic particles upward when the magnetic member is at the reversing position, and then the iris diaphragm is opened.

14. The sample analyzer according to claim 1, wherein the magnetic field applier is further configured to locate the cartridge in proximity of the magnetic member.

15. The sample analyzer according to claim 1, wherein the measurer is an optical measurer comprising a light source configured to generate a light incident on the cartridge and a light receiver configured to receive the light emitted from the cartridge; and
the analyzing processor is further configured to analyze and process a result of a measurement by the optical measurer.

16. The sample analyzer according to claim 1, wherein the measurer comprises:
an imager configured to take an image of the cartridge; and
an optical measurer comprising a light source configured to generate light incident on the cartridge and a light receiver configured to receive the light emitted from the cartridge,
wherein the analyzing processor is further configured to analyze and process the image taken by the imager and/or a result of a measurement by the optical measurer.

17. The sample analyzer of claim 1, wherein the magnetic member is other than an electromagnet.

* * * * *